(12) United States Patent
Sowder et al.

(10) Patent No.: US 8,509,910 B2
(45) Date of Patent: Aug. 13, 2013

(54) TELEMETRY DURING SAFETY MODE OPERATION

(75) Inventors: Conrad L. Sowder, Minneapolis, MN (US); Thomas J. Harris, Shoreview, MN (US); Douglas J. Gifford, Ham Lake, MN (US); William J. Linder, Golden Valley, MN (US); Hiten J. Doshi, Plymouth, MN (US); Scott R. Stubbs, Maple Grove, MN (US); Kenneth P. Hoyme, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 894 days.

(21) Appl. No.: 12/328,454

(22) Filed: Dec. 4, 2008

(65) Prior Publication Data

US 2009/0157127 A1    Jun. 18, 2009

Related U.S. Application Data

(60) Provisional application No. 61/007,835, filed on Dec. 14, 2007.

(51) Int. Cl.
*A61N 1/02*        (2006.01)

(52) U.S. Cl.
USPC ............................................. 607/60; 607/32

(58) Field of Classification Search
USPC ......................................... 607/14, 30–32, 60
See application file for complete search history.

(56) References Cited

U.S. PATENT DOCUMENTS

| | | | |
|---|---|---|---|
| 5,228,450 A * | 7/1993 | Sellers | 600/524 |
| 6,574,510 B2 | 6/2003 | Von Arx et al. | |
| 6,678,560 B1 | 1/2004 | Gilkerson et al. | |
| 6,687,543 B1 * | 2/2004 | Isaac et al. | 607/16 |
| 6,738,670 B1 * | 5/2004 | Almendinger et al. | 607/60 |
| 6,985,773 B2 | 1/2006 | Von Arx et al. | |
| 6,993,393 B2 | 1/2006 | Von Arx et al. | |
| 7,209,790 B2 | 4/2007 | Thompson et al. | |
| 2006/0030902 A1 | 2/2006 | Quiles et al. | |
| 2006/0116744 A1 | 6/2006 | Von Arx et al. | |
| 2007/0239231 A1 * | 10/2007 | Ginggen | 607/63 |

* cited by examiner

*Primary Examiner* — Rex R Holmes
(74) *Attorney, Agent, or Firm* — Schwegman Lundberg & Woessner, P.A.

(57) ABSTRACT

This document discusses, among other things, an implantable device comprising a communication circuit configured to communicate with an external device, a logic circuit communicatively coupled to the communication circuit, and a processor, communicatively coupled to the logic circuit and the communication circuit. The processor is configured to communicate information with the external device, via the communication circuit and the logic circuit, using a set of communication messages. While in a device safety mode, the processor is held in an inactive state and the logic circuit is configured to communicate with the external device using a subset of the set of communication messages.

16 Claims, 3 Drawing Sheets

TELEMETRY DURING SAFETY MODE OPERATION

CLAIM OF PRIORITY

This non-provisional application claims the benefit of priority under 35 U.S.C. §119(e) to U.S. Provisional Patent Application Ser. No. 61/007,835, filed Dec. 14, 2007, the specification of which is herein incorporated by reference in its entirety.

BACKGROUND

Implantable medical devices (IEDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of two or more such capabilities. The devices can be used to treat patients using electrical or other therapy or to aid a physician or caregiver in patient diagnosis through internal monitoring of a patient's condition. The devices can include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability. It is desirable to a physician to tailor a device to a specific patient's condition.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

Figure 1:
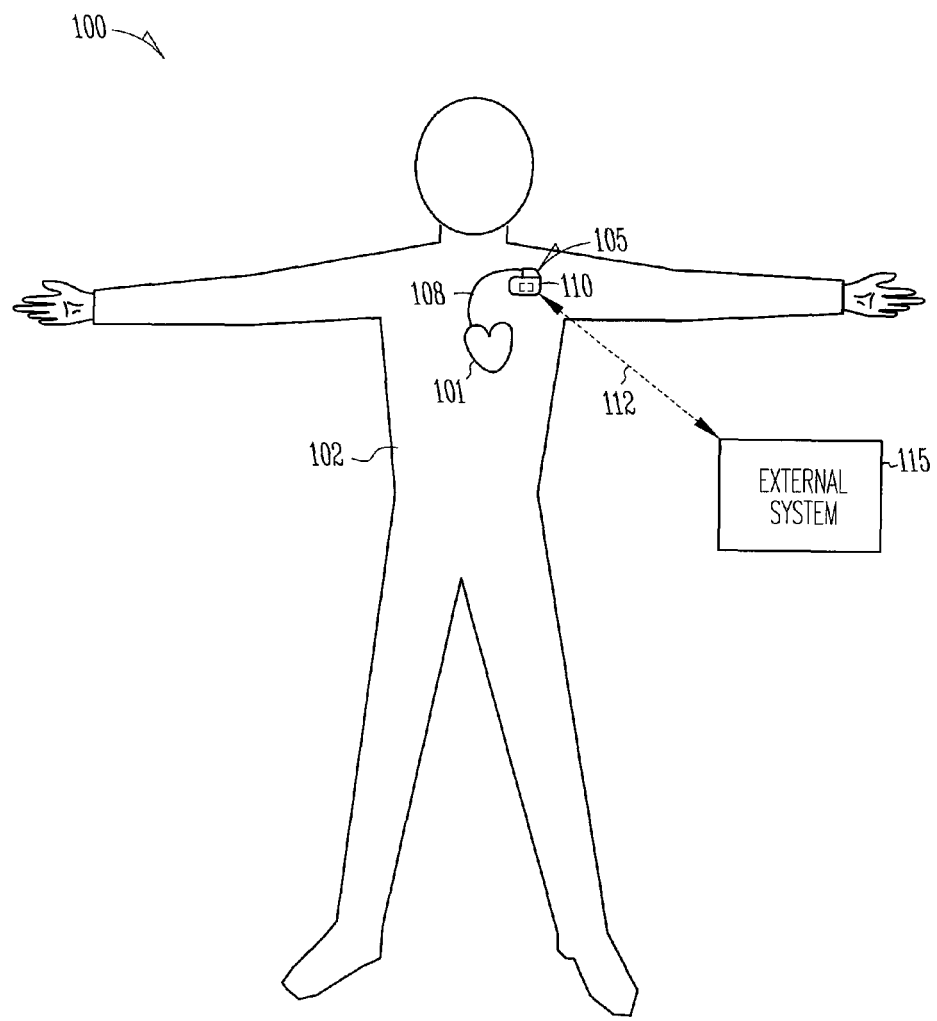
FIG. 1 is an illustration of an example of a cardiac function management (CFM) system.

FIG. 1 is an illustration of an example of a cardiac function management (CFM) system 100 and portions of an environment in which system 100 is used. System 100 includes an implantable system 105, an external system 115, and a telemetry link 112 providing for communication between implantable system 105 and external system 115.

Implantable system 105 includes, among other things, implantable medical device 110 and lead system 108. In various examples, implantable medical device 110 is an implantable CFM device including one or more of a pacemaker, a cardioverter/defibrillator, a cardiac resynchronization therapy (CRT) device, a cardiac remodeling control therapy (RCT) device, a neurostimulator, a drug delivery device or a drug delivery controller, and a biological therapy device. As illustrated in FIG. 1, implantable medical device 110 is implanted in a body 102. In various examples, lead system 108 includes leads for sensing physiological signals and delivering pacing pulses, cardioversion/defibrillation shocks, neurostimulation, pharmaceutical agents, biological agents, and/or other types of energy or substance for treating cardiac disorders. In various examples, electrodes placed in a heart 101 or other portions of body 102 are used to sense physiological signals and deliver pacing pulses, cardioversion/defibrillation shocks, neurostimulation, pharmaceutical agents, biological agents, and/or other types of energy or substance for treating cardiac disorders. In an example, lead system 108 includes one or more pacing-sensing leads each including at least one electrode placed in or on heart 101 for sensing one or more electrograms or delivering pacing pulses. In a specific example, lead system 108 allows pacing pulses to be delivered to multiple atrial and ventricular sites.

Implantable medical device 110 includes a hermetically sealed "can" to house electronic circuitry that performs sensing and therapeutic functions. In an example, intermittent pacing system 120 is housed within the hermetically sealed can. In another example, intermittent pacing system 120 includes internal components housed within hermetically sealed can and external components located external to the hermetically sealed can but communicatively coupled to the internal components.

External system 115 allows a user such as a physician or other caregiver or a patient to control the operation of implantable medical device 110 and obtain information acquired by implantable medical device 110. In an example, external system 115 includes a programmer communicating with implantable medical device 110 bi-directionally via telemetry link 112. In another example, external system 115 is a patient management system including an external device communicating with a remote device through a telecommunication network. The external device is within the vicinity of implantable medical device 110 and communicates with implantable medical device 110 bi-directionally via telemetry link 112. The remote device allows the user to monitor or treat a patient from a distant location.

Telemetry link 112 provides for data transmission from implantable medical device 110 to external system 115. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). Telemetry link 112 also provides for data transmission from external system 115 to implantable medical device 110. This includes, for example, programming implantable medical device 110 to acquire physiological data, programming implantable medical device 110 to perform at least one self-diagnostic test (such as for a device operational status), and programming implantable medical device 110 to deliver one or more therapies.

Figure 2:
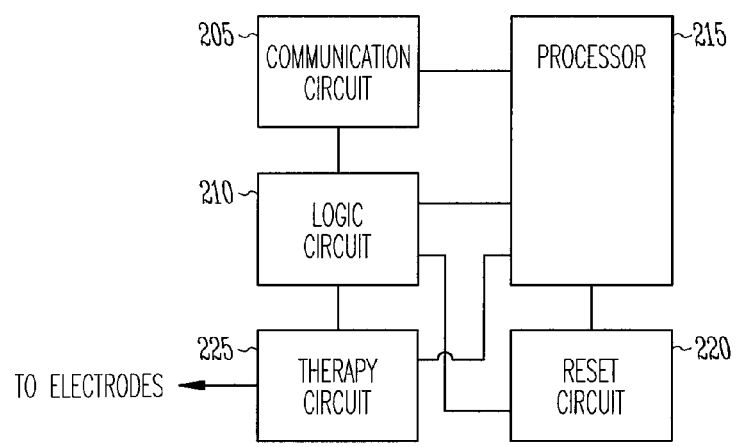
FIG. 2 is a block diagram of portions of an implantable medical device that includes a safety mode operation.

FIG. 2 is a block diagram of an example of portions of an implantable medical device 200 that includes a safety mode operation. The implantable medical device 200 may include a logic circuit 210, a processor 215, and a communication circuit 205 to communicate with an external device. The logic circuit 210 can include hardware circuits or firmware. In some examples, the logic circuit 210 includes a state machine. The processor 215 can include a microcontroller, a microprocessor, a digital signal processor, an application specific integrated circuit (ASIC), a field programmable gate array (FPGA), or any combination thereof. The communication circuit 205, the logic circuit 210, and the processor 215 are communicatively coupled. They are arranged to communicate using electrical signals to influence their operation. In some examples, they are coupled directly and in some examples, they communicate electrical signals through intermediate circuits.

The processor 215 communicates information with external device using a set of communication messages. For example, the set can include messages to accept blocks of data from the external device and to send blocks of data to the external device. The processor 215 communicates the information with the external device via the communication circuit 205 and the logic circuit 210. In some examples, the logic circuit 210 and the communication circuit 205 form data bytes into a communication stream, or message stream, for communicating with the external device. In this way, the logic circuit 210 and the communication circuit 205 can be viewed as a physical layer for the implantable medical device 200. The processor 215 provides data for transmission and the logic circuit 210 and the communication circuit 205 handle the formatting and signal modulation for communicating data with the external device.

The implantable medical device 200 can enter a safety mode under some conditions. For example, the implantable medical device 200 can include a memory error detection circuit to detect memory errors and the implantable medical device 200 enters safety mode when the memory error detection circuit detects errors in processor instruction code or in some critical data area. In some examples, the implantable medical device 200 enters device safety mode based on performance of some particular circuit or circuits. For example, the implantable medical device 200 can include a circuit to detect that the battery is near its end of service, and the implantable medical device 200 enters the safety mode when the battery nears its end of service.

While in the device safety mode, the processor 215 is held in an inactive state, such as a reset state for example. The logic circuit 210 functions as a "safety core" to provide some functionality for the device while the processor 215 is unavailable. In some examples, the logic circuit 210 is included in a mixed mode integrated circuit (IC) that includes both digital and analog circuits, and the mixed mode IC is separate from an IC containing the processor 215.

While in safety mode, the logic circuit 210 is able to communicate with the external device using a subset of the set of communication messages. In some examples, the logic circuit 210 is able to communicate a status message with the external device while the processor is inactive.

Figure 3:
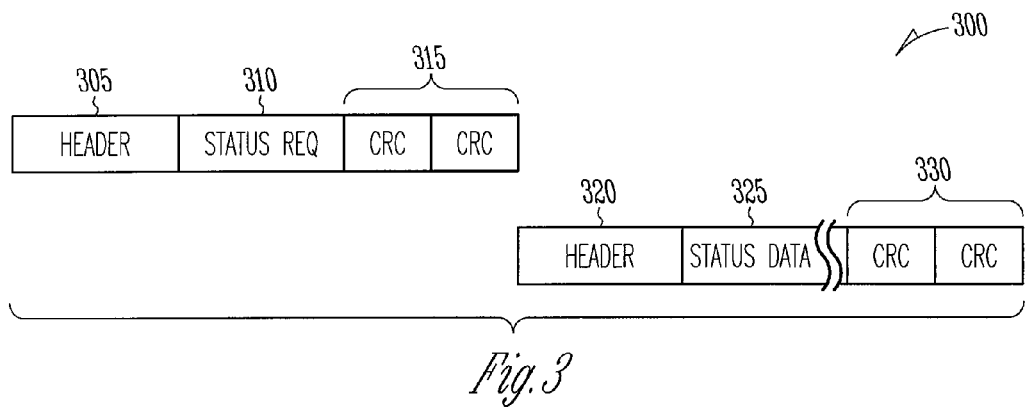
FIG. 3 shows a representation of a status message.

FIG. 3 shows a representation of a status message 300 in which the external device sends a request for status to the implantable medical device 200. The status message 300 is sent serially starting with a header 305. The header 305 indicates the start of the message 300 and may wake up the communication circuit 205. The header 305 is followed by a status request command 310 and the status message may also include two bytes of cyclic redundancy code (CRC) 315 for error detection.

The communication circuit 205 receives the bits of the serial message stream and the logic circuit 210 assembles the stream of data into byte boundaries. The logic circuit 210 decodes the command as a status request. Upon decoding the status request command 310 and without interaction from the inactive processor 215, the logic circuit 210 begins transmitting the response to the status request command 310.

The status response message is sent serially to the external device beginning with a header 320. The logic circuit 210 retrieves one or more bytes of status data 325 from a status storage area and provides them to the communication circuit 205 to be transmit serially. In some examples, the logic circuit 210 assembles ten bytes of device status into the status response message. In some examples, the status response message includes two bytes of CRC 330 at the end of the message. The header 320 information may include identification information such as device serial number for example.

In some examples, the implantable medical device 200 includes a reset circuit 220 that provides a systematic reset to the implantable medical device 200. The reset circuit 200 makes sure the implantable medical device 200 is brought to known state in a systematic fashion. In some examples, the subset of communication messages while in safety mode includes a reset message.

Figure 4:
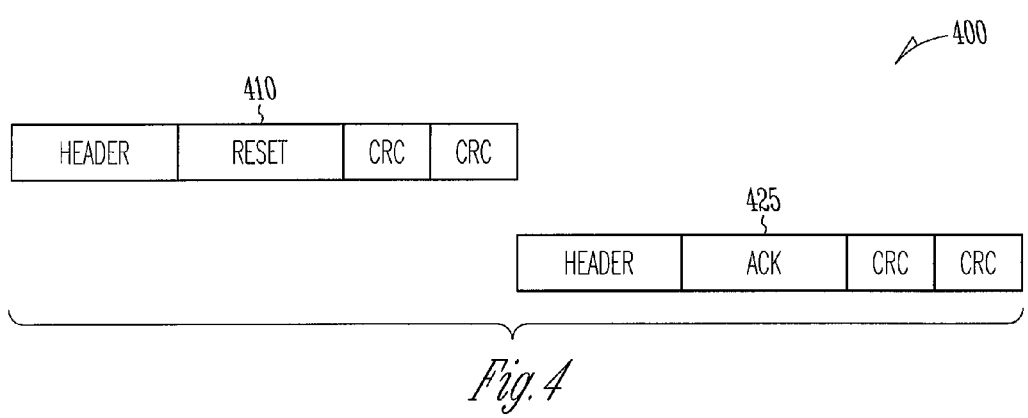
FIG. 4 shows a representation of a reset message.

FIG. 4 shows a representation of a reset message 400 in which the external device sends a reset command 410 to the implantable medical device 200. The logic circuit 210 receives the reset message via the communication circuit 205 and decodes the reset command 410. The logic circuit 210 then triggers a reset of the implantable medical device 200 via the reset circuit 220. In some examples, the logic circuit 210 sends an acknowledge message to the external device that the reset message was received. The acknowledge message is sent serially to the external device and may begin with a header. The logic circuit 210 provides an acknowledge code 425 to the communication circuit 205 to be transmit serially to the external device. The acknowledge message may include CRC.

In some examples, the implantable medical device 200 includes a therapy circuit 225. The therapy circuit 225 provides electrical cardioversion and/or defibrillation stimulation energy using at least two implantable electrodes. One of the electrodes can be incorporated into an implantable housing of the implantable medical device 200. While in safety mode, the logic circuit 210 is able to provide limited control of therapy activities. In some examples, the subset of communication messages while in safety mode includes a message to change the therapy mode of the implantable medical device 200.

Figure 5:
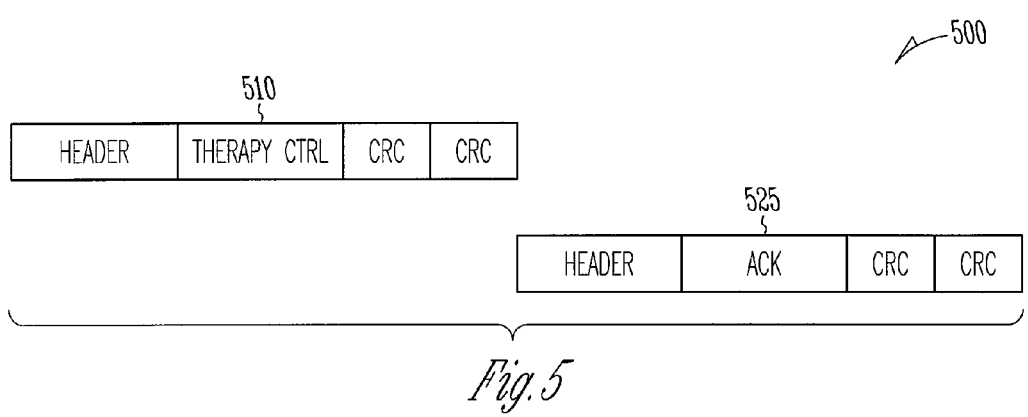
FIG. 5 shows a representation of a therapy control request message.

FIG. 5 shows a representation of a therapy control request message 500. The external device sends a therapy control command 510 to the implantable medical device 200 which is decoded by the logic circuit 210. In some examples, the therapy control command 510 includes a first byte to identify the type of command and a second byte that is decoded by the logic circuit 210 to determine the action to be taken. In some examples, the type of command and the action to be taken are encoded in the same byte which is decoded by the logic circuit 210.

In certain examples, the therapy control request message 500 disables the implantable medical device 200 from providing cardioversion and/or defibrillation therapy. The external device sends the therapy disable message to the implantable medical device 200. The logic circuit 210 receives the therapy disable message via the communication circuit 205 and decodes the message to disable the therapy circuit 225. The logic circuit 210 provides an acknowledge code 525 to the communication circuit 205 to be transmitted serially.

In certain examples, the therapy control request message 500 disables an audio indication of the cardioversion and/or defibrillation therapy. The external device sends the audio indication disable message to the implantable medical device 200. The logic circuit 210 receives the audio indication disable message via the communication circuit 205 and decodes the message to disable the therapy audio indication. The logic circuit 210 may then transmit an acknowledge message via the communication circuit 205.

The above examples show that the implantable medical device 200 is still able to provide some telemetry functionality while in a safety mode, even if the processor 215 is inactive or otherwise disabled. In some examples, the implantable medical device includes tiers of functionality while in safety mode. These tiers of functionality gradually phase out device functionality depending on the condition that triggered the safety mode or when the implantable medical device 200 gradually loses functionality such as from a depleting battery. These tiers of functionality can include one of, or combinations of, the communication messages described in the examples herein. In some examples, one of tiers includes no telemetry functionality.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description, with each claim standing on its own as a separate example. The scope of the invention should be determined with reference to the appended claims, along with the full scope of equivalents to which such claims are entitled.

What is claimed is:

1. An implantable device comprising:
   a therapy circuit configured to provide a therapy to a subject according to a therapy mode;
   a communication circuit configured to communicate with an external device via a telemetry link;
   a logic circuit communicatively coupled to the communication circuit; and
   a processor, communicatively coupled to the logic circuit and the communication circuit, wherein the processor is configured to communicate information with the external device, via the communication circuit and the logic circuit, using a set of communication messages, and
   wherein, while in a device safety mode entered in response to detecting an error of the implantable device, the processor is held in an inactive state and the logic circuit is configured to:
      detect a therapy control request message from the external device, wherein the therapy control request message indicates an action to be taken by the logic circuit;
      change the therapy mode of the implantable device according to the indicated action;
      communicate with the external device using a subset of the set of communication messages; and
      reduce functionality of the implantable device according to tiers of functionality, wherein a first tier of reduced functionality includes reduced therapy functionality and reduced communication functionality, and a second tier of reduced functionality includes no communication functionality.

2. The implantable device of claim 1, wherein, while in the device safety mode, the logic circuit is configured to:
   detect a request for status message from the external device; and
   communicate status information to the external device.

3. The implantable device of claim 1, wherein, while in the device safety mode, the logic circuit is configured to:
   detect a reset message from the external device;
   initiate a reset of the implantable device upon detecting the reset message; and
   communicate an acknowledge message to the external device indicating that the reset message was received.

4. The implantable device of claim 1, wherein the therapy circuit is configured to provide at least one of cardioversion therapy and defibrillation therapy, and wherein the logic circuit is configured to disable the therapy circuit according to the indicated action.

5. An implantable device comprising:
   a therapy circuit configured to provide a therapy to a subject according to a therapy mode, wherein the implantable device is configured to provide an audio indication of the therapy;

a communication circuit configured to communicate with an external device via a telemetry link;

a logic circuit communicatively coupled to the communication circuit; and a processor, communicatively coupled to the logic circuit and the communication circuit, wherein the processor is configured to communicate information with the external device, via the communication circuit and the logic circuit, using a set of communication messages, and wherein, while in a device safety mode entered in response to detecting an error of the implantable device, the processor is held in an inactive state and the logic circuit is configured to:

detect a therapy control request message from the external device, wherein the therapy control request message indicates an action to be taken by the logic circuit;

change the therapy mode of the implantable device according to the indicated action;

disable the audio indication according to the indicated action;

communicate with the external device using a subset of the set of communication messages.

6. A method comprising:

communicating information via a telemetry link between a processor of an implantable device and an external device using a set of communication messages, wherein the implantable device is a cardiac function management (CFM) device that provides electrical therapy to a subject according to a therapy mode;

inactivating the processor while the implantable device is in a device safety mode, wherein the device safety mode is entered in response to detecting an error of the implantable device;

communicating information between the external device and a logic circuit of the implantable device using a subset of the set of communication messages while the implantable device is in the device safety mode, including communicating a message to change the therapy mode of the implantable device; and reducing functionality of the implantable device according to tiers of functionality while the implantable device is in the device safety mode, wherein a first tier of reduced functionality includes reduced therapy functionality and reduced communication functionality, and a second tier of reduced functionality includes no communication functionality.

7. The method of claim 6, wherein communicating information using a subset of communication messages includes communicating a message that contains status information regarding the implantable device.

8. The method of claim 6, wherein communicating information using a subset of communication messages includes communicating a message that causes the implantable device to reset.

9. The method of claim 6, wherein communicating a message to change the therapy mode includes communicating a therapy control request message to the logic circuit to disable the implantable device from providing at least one of cardioversion therapy and defibrillation therapy.

10. A method comprising:

communicating information via a telemetry link between a processor of an implantable device and an external device using a set of communication messages, wherein the implantable device is a cardiac function management (CFM) device that provides electrical therapy to a subject according to a therapy mode;

inactivating the processor while the implantable device is in a device safety mode, wherein the device safety mode is entered in response to detecting an error of the implantable device;

communicating information between the external device and a logic circuit of the implantable device using a subset of the set of communication messages while the implantable device is in the device safety mode, including communicating one or more messages to change the therapy mode of the implantable device and to disable an audio indication provided by the implantable device during the therapy mode.

11. A system comprising:

an implantable cardiac function management (CFM) device and an external device to communicate with the implantable CFM device, wherein the implantable CFM device includes:

a therapy circuit configured to provide a therapy to a subject according to a therapy mode;

a communication circuit configured to communicate via a telemetry link with an external device;

a logic circuit communicatively coupled to the communication circuit; and a processor, communicatively coupled to the logic circuit and the communication circuit, wherein the processor is configured to communicate information with the external device, via the communication circuit and the logic circuit, using a set of communication messages, and wherein, while in a device safety mode entered in response to detecting an error of the implantable device, the processor is held in an inactive state and the logic circuit is configured to communicate with the external device using a subset of the set of communication messages, including a message to change the therapy mode of the implantable device; and reduce functionality of the implantable device according to tiers of functionality, wherein a first tier of reduced functionality includes reduced therapy functionality and reduced communication functionality, and a second tier of reduced functionality includes no communication functionality.

12. The system of claim 11, wherein the external device includes a CFM device programmer.

13. The system of claim 11, wherein the external device is included in a patient management system and is configured to communicate information bi-directionally between the implantable CFM device and a remote third device via a telecommunications network.

14. The system of claim 11, wherein the external device is configured to communicate a request for status message to the implantable CFM device while the implantable CFM device is in the device safety mode and the processor is in the inactive state, and wherein the logic circuit of the implantable CFM device is configured to:

detect the request for status message from the external device; and communicate status information to the external device.

15. The system of claim 11, wherein the external device is configured to communicate a reset message to the implantable CFM device while the implantable CFM device is in the device safety mode, and wherein the logic circuit of the implantable CFM device is configured to:

detect a reset message from the external device;

initiate a reset of the implantable CFM device upon detecting the reset message; and communicate an acknowledge message to the external device indicating that the reset message was received.

16. The system of claim 11, wherein the external device is configured to communicate a therapy control command to the implantable CFM device while the implantable CFM device is in the safety mode, and wherein the logic circuit is configured to:

determine an action from the therapy control command; and change a therapy mode of the implantable CFM device according to the determined action.

* * * * *